March 5, 1963 W. L. SPANDIKOW Plant Pat. 2,232

ROSE PLANT

Filed Oct. 17, 1961

WITNESS

Addison E. Avery

INVENTOR

WILLIAM L. SPANDIKOW by Rummler & Snow

ATTYS.

United States Patent Office

Plant Pat. 2,232
Patented Mar. 5, 1963

2,232

ROSE PLANT

William L. Spandikow, 420 Morton St., Batavia, Ill.

Filed Oct. 17, 1961, Ser. No. 145,785
1 Claim. (Cl. 47—61)

This invention concerns a new and distinct variety of rose plant developed by me at my breeding grounds in Batavia, Illinois, with the object of obtaining a commercially advantageous rose plant having large blooms of an attractive combination of soft, bi-color, red and pink shades, borne singly on relatively long, strong stems, and having good lasting qualities both on the plant and as a cut flower.

I have accomplished these objects in the present new variety, which is the result of definite breeding efforts carried on by me and under my direction at my said breeding grounds since 1957, the new variety originating as a selected seedling produced by a cross between "Golden Rapture" (Plant Patent No. 1,413) as the seed parent and "Happiness" (Plant Patent No. 911) as the pollen parent.

The new variety was observed to have the continuous blooming habit of its parents, "Happiness" and "Golden Rapture," with the added advantage of producing more blooms than either parent, during the winter months and having very double flowers with about fifteen percent more petals than the average run of "Happiness." Also the new variety was tested at my said breeding grounds and observed to be unaffected by wet or hot weather and to be resistant to mildew and black spot, prevalent among other roses grown with my new variety in the Batavia, Illinois area.

My new variety has been asexually reproduced by me at Batavia, Illinois, by budding and extensive propagation by budding has demonstrated the novel characteristics of the new plant to hold true, from generation to generation, and to be firmly fixed.

The novel and distinctive color characteristics of my new variety of rose plant are illustrated in the accompanying full color drawings in which.

Figures 1, 2, 3:
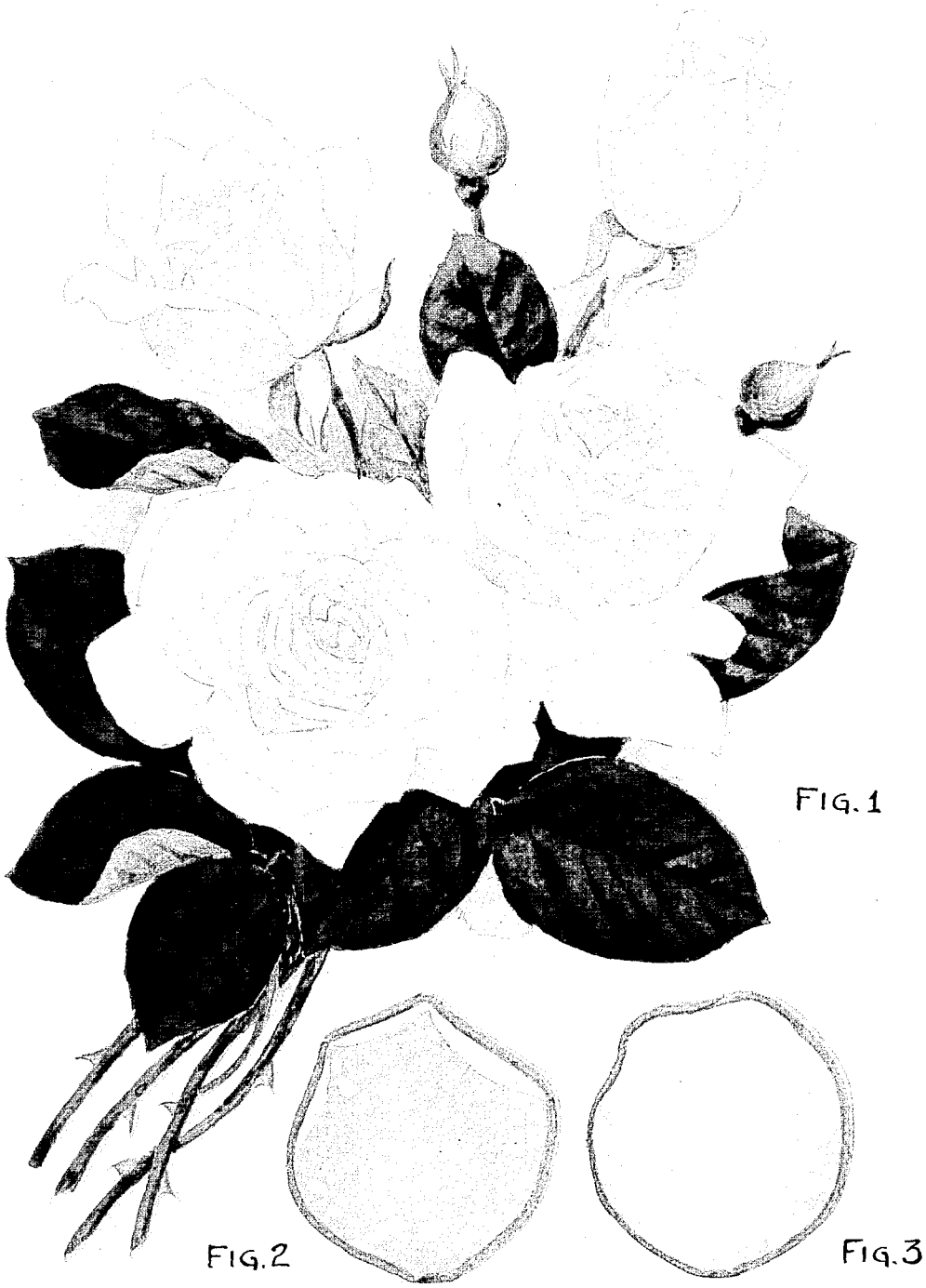
FIGURE 1 shows the foliage and wood, as well as various stages of the bloom from new bud to fully matured flowers.
FIG. 2 is a view showing the reverse face of an outer petal from the fully opened flower.
FIG. 3 is a view of the front or inside face of the same petal.

Other features of novelty in my new variety of rose plant will appear more particularly in the following detailed description of the new plant:

*The Plant*

Origin: Selected seedling.
Parentage:
*Seed parent.*—"Golden Rapture" (P.P. 1,413).
*Pollen parent.*—"Happiness" (P.P. 911).
Classification: Hybrid tea.
Form: Bush.
Height: 3 to 4 feet.
Growth: Vigorous, sturdy, and upright.
Foliage: Abundant in quantity with compound leaves having 3–7 serrate, ovate leaflets.
*Size of leaf.*—Similar to "Happiness."
*Texture.*—Leathery and dull. Plant has many thorns.

*Bud*

Form: Pointed, long.
Size: Medium large.
Color: Red pink, where sepals first divide.
Sepals: Partly foliaceous, hooded over bud.
Calyx: Pear shaped, smooth, and does not split.
Peduncle: Long and heavy.

*Flower*

Blooms: Continuously and profusely, 20 to 25 blooms on one plant.
Size: Very large. 5½ inches in diameter, 3 inches in depth.
Borne: Singly, on long, strong stems.
Shape: High centered. Form does not change as flower matures.
Petalage: 35 to 40 petals arranged in imbricated rows.
Color:
*Central petals.*—Dark pink.
*Outer rows of petals.*—Inner face—pink to pale-pink, at margins, turning to light silver pink as full bloom ages; light yellow at base. Outer face—yellow at base—to light pink to dark pink at margins.
Texture of petals: Leathery. Appearance—velvety.
Persistence: Petals stay on stem for the life of the flower. Flower hangs on and dries, is unaffected by wet or hot weather.
Lasting quality: Good, on plant and as a cut flower.

The novel color characteristics of my new variety of rose plant, according to Maerz and Paul Dictionary of Color, are as follows:

| | Plate | Letter | Number |
|---|---|---|---|
| Flower: | | | |
| Outer petals—inner face— | | | |
| Palest Pink at tips | 1 | C | 1 |
| To Pink | 1 | F | 9 |
| Yellow at base (Fig. 3) | 9 | L | 2 |
| Outer petals—outer or back face— | | | |
| Pink | 1 | G | 3 |
| To Dark Pink | 1 | I | 9 |
| Yellow at base (Fig. 2) | 9 | K | 6 |
| Innermost petals—Dark Pink | 1 | K | 9 |
| To | 1 | L | 9 |
| Stem: Green | 21 | L | 5 |
| Thorns | 22 | J | 1 |
| Leaves: | | | |
| Top side—Green | 23 | L | 8 |
| Under side—Green | 21 | I | 7 |

In general, except for the blooms, my new variety of rose plant most nearly resembles "Happiness" in the character of its foliage, the length and size of the stems, and the nature of its growth habits. The new variety produces more blooms than "Happiness" in the winter seasons, as a green house plant, and the blooms have a larger number of petals. Also the stems are of a lighter green in color than those of "Happiness."

The particularly distinctive feature of the new variety, however, resides in the coloring of its blooms which are generally of a soft pink in the partially opened buds, the outer rows of petals changing continuously, on the inner face of the petals, to an almost white pink as the bloom opens fully and matures, the innermost petals remaining almost solid pink. The blooms, thus, are a combination of pink and pink-white, the pink being predominant in the partly opened flower and at the center of the fully opened bloom and the white appearing at the margins of the partly opened outer petals and spreading inwardly toward the base of the petals of the successive rows as the bloom ages. The outer face of all of the petals, however, remains predominantly pink.

Having thus disclosed my new variety of rose plant, I claim:

A new and distinct variety of rose plant of the hybrid tea type, substantially as herein shown and described, characterized as to novelty by the continuously changing pink and white color of its blooms, wherein the freshly opened buds are mainly a soft pink with pink-white margins on the inner face of the outermost petals, and wherein as the bloom fully opens and matures the pink-white coloring spreads toward the base of the petals, in row after row thereof, until all but the center rows of petals have a pink-white appearance from the inner face of the bloom; the reverse face of the petals remaining an over-all pink in color, and there being a light yellow color at the base of the petals on both the inside and outside surfaces thereof.

No references cited.